(12) United States Patent
Schroeder et al.

(10) Patent No.: US 9,895,300 B2
(45) Date of Patent: Feb. 20, 2018

(54) MILD COSMETIC CLEANING AGENT

(71) Applicant: Henkel AG & Co. KGaA, Duesseldorf (DE)

(72) Inventors: Thomas Schroeder, Hamburg (DE); Dirk Hentrich, Hamburg (DE)

(73) Assignee: Henkel AG & Co. KGaA (DE)

( * ) Notice: Subject to any disclaimer, the term of this patent is extended or adjusted under 35 U.S.C. 154(b) by 0 days.

(21) Appl. No.: 15/184,700

(22) Filed: Jun. 16, 2016

(65) Prior Publication Data
US 2016/0287504 A1 Oct. 6, 2016

Related U.S. Application Data

(63) Continuation of application No. PCT/EP2014/074302, filed on Nov. 12, 2014.

(30) Foreign Application Priority Data

Dec. 17, 2013 (DE) .................. 10 2013 226 281

(51) Int. Cl.
*A61K 8/46* (2006.01)
*A61Q 19/10* (2006.01)
*A61K 8/365* (2006.01)
*A61K 8/41* (2006.01)
*A61K 8/44* (2006.01)
*A61K 8/60* (2006.01)
*A61Q 5/02* (2006.01)

(52) U.S. Cl.
CPC ............. *A61K 8/466* (2013.01); *A61K 8/365* (2013.01); *A61K 8/416* (2013.01); *A61K 8/44* (2013.01); *A61K 8/604* (2013.01); *A61Q 5/02* (2013.01); *A61Q 19/10* (2013.01); *A61K 2800/51* (2013.01); *A61K 2800/5922* (2013.01); *A61K 2800/75* (2013.01)

(58) Field of Classification Search
None
See application file for complete search history.

(56) References Cited

U.S. PATENT DOCUMENTS

| | | | | |
|---|---|---|---|---|
| 2012/0213725 | A1* | 8/2012 | Galleguillos | A61K 8/463 424/70.16 |
| 2014/0161754 | A1* | 6/2014 | Arora | A61Q 5/02 424/70.12 |
| 2014/0320956 | A1 | 10/2014 | Taka et al. | |
| 2014/0349902 | A1* | 11/2014 | Allef | A61K 8/361 510/119 |

FOREIGN PATENT DOCUMENTS

| | | |
|---|---|---|
| SG | 185165 A1 | 11/2012 |
| WO | 92/08440 A1 | 5/1992 |
| WO | 2011/015857 A2 | 2/2011 |
| WO | 2011/117650 A2 | 9/2011 |
| WO | 2013/093473 A1 | 6/2013 |

OTHER PUBLICATIONS

PCT International Search Report (PCT/EP2014/074302) dated Mar. 23, 2015.

* cited by examiner

*Primary Examiner* — Necholus Ogden, Jr.
(74) *Attorney, Agent, or Firm* — David K. Benson

(57) ABSTRACT

A particularly mild, highly foaming, and conditioning cosmetic cleansing agent includes, in a suitable carrier, a) at least one anionic surfactant according to the following formula (I), in which the radicals $R^2$ to $R^5$ each represent a hydrogen atom, and b) at least one anionic surfactant according to the following formula (I), in which at least one of the radicals $R^2$ to $R^5$ represents a $C_1$-$C_4$ alkyl radical and the other radicals independently of one another represent a hydrogen atom or a $C_1$-$C_4$ alkyl radical, wherein $R^1$ in each case represents a linear or branched, saturated or unsaturated alkyl radical having 6 to 30 carbon atoms, and $M^+$ in each case represents an ammonium cation, an alkanol ammonium cation or a metal cation.

7 Claims, No Drawings

MILD COSMETIC CLEANING AGENT

FIELD OF THE INVENTION

The present invention generally relates to cosmetics, and more particularly relates to mild cleansing agents which include a specific surfactant mixture.

BACKGROUND OF THE INVENTION

Cosmetic cleansing agents, such as hair shampoos for example, are based on conventional anionic, amphoteric, zwitterionic, non-ionic and/or cationic surfactants.

Due to their excellent cleansing and foaming performance, anionic surfactants are predominantly used, optionally in a mixture with small amounts of co-surfactants. Typical anionic surfactants which are used in many commercially available shampoos are alkyl sulfates or alkyl ether sulfates. Alkyl ether sulfates are usually preferred since they are milder and have an outstanding foaming performance.

When formulating particularly mild cleansing compositions for use on sensitive areas of skin (such as the skin of the face for example), for use on baby skin or for use on sensitive and/or damaged hair, alkyl ether sulfates are not always satisfactory since they can have too high an irritation potential and can cause damaged hair to become increasingly brittle.

In the past, therefore, numerous attempts have been made to find particularly mild surfactant mixtures which have sufficiently high foam quantities and qualities, and which have no or only a slight potential for causing irritation to the skin and/or mucous membranes. The surfactant mixtures should moreover be suitable for use in hair treatment agents, specifically for use in hair cleansing agents with good care properties.

In the application WO 92/08440, mild surfactant mixtures having excellent foam properties are disclosed, which include a mixture of acyl isethionates, zwitterionic surfactants and alkyl ether sulfates. WO 11/015857 discloses cleansing compositions with a low potential for causing irritation to the skin, which include novel $C_{5-30}$ alkoyl alkyl isethionates and amphoteric surfactants in a weight ratio of 4:1 to 1:4. The mild cleansing agents are suitable for use as a baby shampoo.

One disadvantage of many mild skin and hair cleansing agents is that the better skin tolerability thereof is often at the expense of the texture of the cleansing agents.

Also disadvantageous are the often unsatisfactory foam amounts and foam properties which can be achieved with mild hair cleansing agents. In addition, it has been observed that the care properties of mild cleansing agents (particularly on the hair) are not always satisfactory.

It is therefore desirable to produce particularly mild cosmetic cleansing agents which are well-tolerated by the skin and mucous membranes. The cleansing agents should have a user-friendly texture and should, in conjunction with water, produce a large amount of foam. The cleansing agents should also have improved care properties.

Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

A cosmetic cleansing agent that includes, in a suitable carrier, at least one anionic surfactant according to the following formula (I), in which the radicals $R^2$ to $R^5$ each represent a hydrogen atom; and at least one anionic surfactant according to the following formula (I), in which at least one of the radicals $R^2$ to $R^5$ represents a $C_1$-$C_4$ alkyl radical and the other radicals independently of one another represent a hydrogen atom or a $C_1$-$C_4$ alkyl radical,

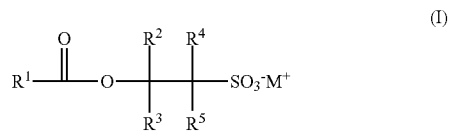

(I)

wherein $R^1$ in each case represents a linear or branched, saturated or unsaturated alkyl radical having 6 to 30 carbon atoms, and $M^+$ in each case represents an ammonium cation, an alkanol ammonium cation or a metal cation.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

A first aspect of the invention is a cosmetic cleansing agent that includes, in a suitable carrier,
a) at least one anionic surfactant according to the following formula (I), in which the radicals $R^2$ to $R^5$ each represent a hydrogen atom, and
b) at least one anionic surfactant according to the following formula (I), in which at least one of the radicals $R^2$ to $R^5$ represents a $C_1$-$C_4$ alkyl radical and the other radicals independently of one another represent a hydrogen atom or a $C_1$-$C_4$ alkyl radical,

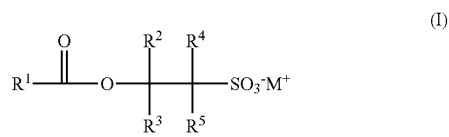

(I)

wherein
  $R^1$ in each case represents a linear or branched, saturated or unsaturated alkyl radical having 6 to 30 carbon atoms, and
  $M^+$ in each case represents an ammonium cation, an alkanol ammonium cation or a metal cation.

A suitable carrier is preferably understood to mean an aqueous or aqueous-alcoholic carrier. The carrier includes preferably at least 50% by weight, more preferably at least 60% by weight and particularly preferably at least 70% by weight water.

Furthermore, the cosmetic carrier may include 0.01 to 40% by weight, preferably 0.05 to 35% by weight and in particular 0.1 to 30% by weight of at least one alcohol which may be selected from ethanol, 1-propanol, 2-propanol, isopropanol, glycerol, diglycerol, triglycerol, 1-butanol, 2-butanol, 1,2-butanediol, 1,3-butanediol, 1-pentanol, 2-pentanol, 1,2-pentanediol, 1,5-pentanediol, 1-hexanol, 2-hexanol, 1,2-hexanediol, 1,6-hexanediol, polyethylene glycols, sorbitol, sorbitan, benzyl alcohol, phenoxyethanol or mixtures of these alcohols. Preference is given to water-soluble alcohols. Particular preference is given to ethanol, 1-propanol, 2-propanol, isopropanol, 1,2-propylene glycol, glycerol, benzyl alcohol and/or phenoxyethanol and mixtures of these alcohols. Glycerol is particularly preferred.

Particularly mild cosmetic cleansing agents having a good foaming behavior were able to be produced when the surfactants a) and b) were used in a particular weight ratio a):b) of approximately 1:2.5 to 4:1.

In a first preferred embodiment, cosmetic cleansing agents according to the invention are characterized in that they include the surfactants a) and b) preferably in a weight ratio a) to b) of 1:2.5 to 4:1, more preferably 1:2 to 3:1, particularly preferably 1:1.5 to 2.5:1 and more particularly preferably 1:1 to 2:1.

Preferred anionic surfactants a) of the abovementioned formula (I) have as the radical $R^1$ a linear or branched, saturated or unsaturated alkyl radical having 8 to 18 carbon atoms. With particular preference, the radical $R^1$ represents a $C_8$, $C_{10}$, $C_{12}$, $C_{14}$, $C_{16}$ radical or mixtures of these fatty acid radicals as are obtained when the fatty acid(s) is/are derived from natural oils such as coconut oil for example.

In preferred anionic surfactants a) according to formula (I), $M^+$ preferably represents an alkali metal cation or an ammonium ion, particularly preferably a potassium ion or a sodium ion and more particularly preferably a sodium ion.

Very particularly preferred anionic surfactants a) according to the abovementioned formula (I) are the compounds known under the INCI names Sodium Cocoyl Isethionate, Potassium Cocoyl Isethionate, Ammonium Cocoyl Isethionate, Sodium Lauroyl Isethionate, Potassium Lauroyl Isethionate, Ammonium Lauroyl Isethionate, Sodium Myristoyl Isethionate, Potassium Methyl Isethionate and Ammonium Myristoyl Isethionate. Particular preference is given to Sodium Cocoyl Isethionate and/or Sodium Lauroyl Isethionate. Commercial products of this type are available for example from the companies Clariant or Uniquema under the trade names "Hostapon®" or "Arlatone®".

Preferred anionic surfactants b) of the abovementioned formula (I) have as the radical $R^1$ a linear or branched, saturated or unsaturated alkyl radical having 8 to 18 carbon atoms. With particular preference, the radical $R^1$ represents a $C_8$, $C_{10}$, $C_{12}$, $C_{14}$, $C_{16}$ radical or mixtures of these fatty acid radicals as are obtained when the fatty acid(s) is/are derived from natural oils such as coconut oil for example.

In preferred anionic surfactants b) according to formula (I), $M^+$ preferably represents an alkali metal cation or an ammonium ion, particularly preferably a potassium ion or a sodium ion and more particularly preferably a sodium ion.

In particularly preferred anionic surfactants b) according to the abovementioned formula (I), the radicals $R^2$ to $R^5$ each represent a methyl, ethyl, n-propyl, n-butyl or 2-butyl group.

Preferably, at least one of the radicals $R^2$ to $R^5$ represents a methyl, ethyl or n-propyl group, and in particular a methyl group.

In one particularly preferred embodiment, just one of the radicals $R^2$ to $R^5$ represents a $C_1$-$C_4$ alkyl group—in particular a methyl group—and the other radicals each represent a hydrogen atom.

In principle, it is also possible that the anionic surfactant b) according to formula (I) includes an isomer mixture that includes both components which have for example a $C_1$-$C_4$ alkyl group—in particular a methyl group—as the radical $R^2$ and a hydrogen group as each of the radicals $R^3$ to $R^5$ and components which have for example a $C_1$-$C_4$ alkyl group—in particular a methyl group—as the radical $R^5$ and a hydrogen group as each of the radicals $R^2$ to $R^4$.

Very particularly preferred anionic surfactants b) of the abovementioned formula (I) are the compounds known under the INCI names Sodium Cocoyl Methyl Isethionate, Potassium Cocoyl Methyl Isethionate, Ammonium Cocoyl Methyl Isethionate, Sodium Lauroyl Methyl Isethionate, Potassium Lauroyl Methyl Isethionate, Ammonium Lauroyl Methyl Isethionate, Sodium Myristoyl Methyl Isethionate, Potassium Myristoyl Methyl Isethionate and Ammonium Myristoyl Methyl Isethionate.

Particular preference is given to Sodium Cocoyl Methyl Isethionate and/or Sodium Lauroyl Methyl Isethionate. Commercial products of this type are available for example from the company Innospec under the trade name "Iselux® LQ-CLR-SB".

In a second preferred embodiment, cosmetic cleansing agents according to the invention are characterized in that they include
  a) at least one anionic surfactant according to formula (I), in which the radicals $R^2$ to $R^5$ each represent a hydrogen atom, and
  b) at least one anionic surfactant according to formula (I), in which at least one of the radicals $R^2$ to $R^5$ represents a methyl radical and the other radicals represent a hydrogen atom,
  with the proviso that
    $R^1$ in each case represents a linear or branched, saturated or unsaturated alkyl radical having 8 to 18 carbon atoms, and
    $M^+$ in each case represents a sodium ion, potassium ion or ammonium ion.

Within this embodiment, particular preference is given to cosmetic cleansing agents according to the invention which include
  a) at least one of the anionic surfactants known under the INCI names Sodium Cocoyl Isethionate or Sodium Lauroyl Isethionate, and
  b) at least one of the anionic surfactants known under the INCI names Sodium Lauroyl Methyl Isethionate or Sodium Cocoyl Methyl Isethionate.

The cosmetic cleansing agents according to the invention may include the surfactants a) and b) in each case in amounts of 0.5 to 20% by weight, the amounts by weight relating to the total weight of the cleansing agent.

If the surfactants a) and b) are used in each case in amounts of less than 0.5% by weight, the cosmetic cleansing agents do not form a sufficiently high amount of foam. If the surfactants a) and b) are used in each case in amounts of more than 20% by weight, the cleansing agents are no longer sufficiently gentle on the skin.

In a third preferred embodiment, cosmetic cleansing agents according to the invention are therefore characterized in that the proportion by weight of the anionic surfactants a) and b) in the total weight of the composition is preferably in each case 0.5 to 20% by weight, more preferably 0.75 to 15% by weight, particularly preferably 1 to 10% by weight and in particular 1.5 to 7.5% by weight.

One aim of the use according to the invention was to provide particularly mild, highly foaming cosmetic compositions, which was able to be achieved by combining the surfactants a) and b). The amount of foam produced by the agents according to the invention corresponds approximately to the amount of foam which can be achieved with cleansing agents based on alkyl ether sulfates, the agents according to the invention being milder.

The additional use of anionic alkyl ether sulfates in the cleansing agents according to the invention is therefore not necessary. In a further preferred embodiment of the invention, cosmetic cleansing agents according to the invention are therefore characterized in that the proportion by weight of sulfate group-containing surfactants in the total weight of the compositions is preferably less than 0.5% by weight, more preferably less than 0.3% by weight and in particular less than 0.2% by weight.

The amount of foam, the foam properties (in particular the high foam density) and/or the mildness of the compositions according to the invention were on the other hand able to be further increased when specific amphoteric surfactants were added thereto.

In a fourth preferred embodiment, cosmetic cleansing agents according to the invention are therefore characterized in that they additionally include at least one amphoteric surfactant of the following formula (II)

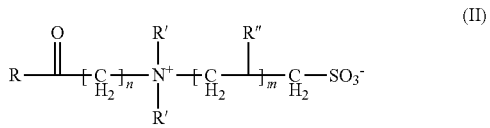

in which
R represents a linear or branched, saturated or unsaturated alkyl radical having 8 to 30 carbon atoms,
R' represents a $C_1$-$C_6$ alkyl or a $C_1$-$C_6$ hydroxyalkyl radical,
R" represents a hydrogen atom, a hydroxyl group, a $C_1$-$C_6$ alkyl or a $C_1$-$C_6$ hydroxyalkyl radical,
the numbers n and m independently of one another represent numbers from 1 to 5,
wherein the proportion by weight of the surfactant according to formula (II) in the total weight of the composition is 1 to 15% by weight.

With particular preference, the proportion by weight of the surfactant according to formula (II) in the total weight of the composition is 2 to 12.5% by weight and very particularly preferably 3 to 10% by weight.

Within this fourth preferred embodiment, particular preference is given to cosmetic cleansing agents which include at least one amphoteric surfactant of the following formula (II), in which
R represents a linear or branched, saturated or unsaturated alkyl radical having 8 to 18 carbon atoms,
R' represents a methyl or ethyl radical, preferably a methyl radical,
R" represents a hydrogen atom or a hydroxyl group, preferably a hydroxyl group, and
n represents a number from 1 to 3, preferably the number 3, and m represents the numbers 1 or 2, preferably the number 1.

Particularly preferred amphoteric surfactants according to formula (II) are known under the INCI name Cocamidopropyl Hydroxysultaine and are available commercially, for example under the names "Mirataine®" from the company Rhodia, "Rewoteric®" from the company Goldschmidt or "Mackam®" from the company The McIntyre Group.

In a fifth preferred embodiment, cosmetic cleansing agents according to the invention are therefore characterized in that they include at least one anionic surfactant a) according to formula (I), at least one anionic surfactant b) according to formula (I) and at least one amphoteric surfactant according to formula (II), wherein
the proportion by weight of the surfactant a) in the total weight of the cleansing agents is preferably 0.5 to 20% by weight, more preferably 0.75 to 15% by weight,
the proportion by weight of the surfactant b) in the total weight of the cleansing agents is preferably 0.5 to 20% by weight, more preferably 0.75 to 15% by weight, and
the proportion by weight of the surfactant according to formula (II) in the total weight of the cleansing agents is preferably 1 to 15% by weight, more preferably 2 to 12.5% by weight.

Particularly preferred cosmetic cleansing agents within this embodiment are characterized in that they include
a) at least one of the anionic surfactants known under the INCI names Sodium Cocoyl Isethionate or Sodium Lauroyl Isethionate,
b) at least one of the anionic surfactants known under the INCI names Sodium Lauroyl Methyl Isethionate or Sodium Cocoyl Methyl Isethionate, and
c) at least one amphoteric surfactant known under the INCI name Cocamidopropyl Hydroxysultaine,
wherein
the proportion by weight of the Sodium Cocoyl Isethionate or of the Sodium Lauroyl Isethionate in the total weight of the cleansing agents is preferably 1 to 10% by weight and in particular 1.5 to 7.5% by weight,
the proportion by weight of the Sodium Lauroyl Methyl Isethionate or of the Sodium Cocoyl Methyl Isethionate in the total weight of the cleansing agents is preferably 1 to 10% by weight and in particular 1.5 to 7.5% by weight, and
the proportion by weight of the Cocamidopropyl Hydroxysultaine in the total weight of the cleansing agents is preferably 3 to 10% by weight.

Besides the amount of foam, the foam properties (in particular the high foam density) and/or the mildness, the care properties of the compositions according to the invention were also able to be further increased if at least one alkyl (oligo)glucoside was added thereto.

In a sixth preferred embodiment, cosmetic cleansing agents according to the invention are therefore characterized in that they additionally include at least one alkyl (oligo) glucoside of general formula RO-$[G]_x$, in which R represents an alkyl and/or alkenyl radical having 4 to 24 C atoms, G represents a sugar residue having 5 or 6 C atoms, and x represents numbers from 1 to 10, wherein the proportion by weight of the alkyl (oligo)glucoside in the total weight of the cleansing agents is preferably 0.5 to 10% by weight.

Preferred alkyl (oligo)glucosides may be selected from compounds of the general formula RO-$[G]_x$, in which [G] preferably derives from aldoses and/or ketoses having 5-6 carbon atoms, preferably from glucose, and in which the radical R preferably represents an alkyl radical having 8, 10, 12, 14, 16 and/or 18 carbon atoms.

The index number x denotes the degree of oligomerization (DP), that is to say the distribution of the mono- and oligoglucosides. The index number x preferably has a value in the range from 1 to 10, particularly preferably in the range from 1 to 3, said index number not being a whole number but rather a fractional number which can be determined analytically.

Particularly preferred alkyl (oligo)glucosides have a degree of oligomerization of between 1.2 and 1.5.

Particularly preferred alkyl (oligo)glucosides are the compounds known under the INCI names Caprylyl/Capryl Glucoside, Decyl Glucoside, Lauryl Glucoside and Coco Glucoside.

With particular preference, the proportion by weight of the aforementioned alkyl (oligo)glucosides in the total weight of the composition is 0.5 to 7.5% by weight and very particularly preferably 0.5 to 5% by weight.

In a seventh preferred embodiment, cosmetic cleansing agents according to the invention are characterized in that they include at least one anionic surfactant a) according to formula (I), at least one anionic surfactant b) according to formula (I), at least one amphoteric surfactant according to formula (II) and at least one alkyl (oligo)glucoside, wherein
- the proportion by weight of the surfactant a) in the total weight of the cleansing agents is preferably 0.5 to 20% by weight, more preferably 0.75 to 15% by weight,
- the proportion by weight of the surfactant b) in the total weight of the cleansing agents is preferably 0.5 to 20% by weight, more preferably 0.75 to 15% by weight,
- the proportion by weight of the surfactant according to formula (II) in the total weight of the cleansing agents is preferably 1 to 15% by weight, more preferably 2 to 12.5% by weight, and
- the proportion by weight of the alkyl (oligo)glucoside in the total weight of the cleansing agents is preferably 0.5 to 10% by weight, more preferably 0.5 to 7.5% by weight.

Particularly preferred cosmetic cleansing agents within this embodiment are characterized in that they include
- a) at least one of the anionic surfactants known under the INCI names Sodium Cocoyl Isethionate or Sodium Lauroyl Isethionate,
- b) at least one of the anionic surfactants known under the INCI names Sodium Lauroyl Methyl Isethionate or Sodium Cocoyl Methyl Isethionate,
- c) at least one amphoteric surfactant known under the INCI name Cocamidopropyl Hydroxysultaine, and
- d) at least one of the compounds known under the INCI names Caprylyl/Capryl Glucoside, Decyl Glucoside, Lauryl Glucoside and Coco Glucoside, wherein
- the proportion by weight of the Sodium Cocoyl Isethionate or of the Sodium Lauroyl Isethionate in the total weight of the cleansing agents is preferably 1 to 10% by weight and in particular 1.5 to 7.5% by weight,
- the proportion by weight of the Sodium Lauroyl Methyl Isethionate or of the Sodium Cocoyl Methyl Isethionate in the total weight of the cleansing agents is preferably 1 to 10% by weight and in particular 1.5 to 7.5% by weight,
- the proportion by weight of the Cocamidopropyl Hydroxysultaine in the total weight of the cleansing agents is preferably 3 to 10% by weight, and
- the proportion by weight of the Caprylyl/Capryl Glucoside, Decyl Glucoside, Lauryl Glucoside or Coco Glucoside in the total weight of the cleansing agents is preferably 0.5 to 5% by weight.

In an eighth preferred embodiment, cosmetic cleansing agents according to the invention are characterized in that they additionally include at least one chelating agent, wherein the proportion by weight of the chelating agent in the total weight of the composition is preferably 0.01 to 3% by weight, more preferably 0.05 to 2% by weight and in particular 0.1 to 1% by weight.

Suitable chelating agents may preferably be selected from aminocarboxylates, aminophosphonates, lactic acid, tartaric acid, citric acid or mixtures thereof.

Particular preference is given to ethylenediaminetetraacetic acid (EDTA) and/or ethylenediamine disuccinate (EDDS). EDDS is particularly preferred on account of its biodegradability.

In a further preferred embodiment, the care properties of the cosmetic agents can be further increased if said cosmetic agents additionally include at least one conditioning active ingredient which may be selected from the group consisting of
- protein hydrolysates,
- cationic polymers,
- vitamins,
- fats, oils and/or waxes,
- glycerol.

Suitable protein hydrolysates are to be understood to mean product mixtures which can be obtained by acid-catalyzed, base-catalyzed or enzyme-catalyzed degradation of proteins. Protein hydrolysates of plant, animal and/or marine origin may be used.

Animal protein hydrolysates are for example hydrolysates of elastin, collagen, keratin, silk and milk protein, which may also be present in the form of salts. Such products are sold for example under the brand names Dehylan® (Cognis), Promois® (Interorgana), Collapuron® (Cognis), Nutrilan® (Cognis), Gelita-Sol® (Deutsche Gelatine Fabriken Stoess & Co), Lexein® (Inolex) and Kerasol® (Croda).

Preference is given to protein hydrolysates of plant origin, for example soy, almond, rice, pea, potato and wheat protein hydrolysates. Such products are available for example under the brand names Gluadin® (Cognis), DiaMin® (Diamalt), Lexein® (Inolex) and Crotein® (Croda).

Use may also be made of cationized protein hydrolysates, wherein the underlying protein hydrolysate may originate from animals, for example from collagen, milk or keratin, from plants, for example from wheat, maize, rice, potatoes, soy or almonds, from marine life forms, for example from fish collagen or algae, or from protein hydrolysates obtained by biotechnology. The protein hydrolysates underlying the cationic derivatives can be obtained from the corresponding proteins by means of a chemical, in particular alkaline or acid hydrolysis, an enzymatic hydrolysis and/or a combination of both types of hydrolysis. The hydrolysis of proteins generally gives rise to a protein hydrolysate having a molecular weight distribution from approximately 100 Daltons up to several thousand Daltons. Preference is given to those cationic protein hydrolysates, the underlying protein component of which has a molecular weight of 100 to 25,000 Daltons, preferably 250 to 5000 Daltons. Cationic protein hydrolysates are also understood to include quaternized amino acids and mixtures thereof. The quaternization of the protein hydrolysates or of the amino acids is often carried out by means of quaternary ammonium salts such as for example N,N-dimethyl-N-(n-alkyl)-N-(2-hydroxy-3-chloro-n-propyl) ammonium halides. The cationic protein hydrolysates may also be further derivatized. As typical examples of the cationic protein hydrolysates and derivatives, mention may be made of the commercially available products known under the INCI names: Cocodimonium Hydroxypropyl Hydrolyzed Collagen, Cocodimonium Hydroxypropyl Hydrolyzed Casein, Cocodimonium Hydroxypropyl Hydrolyzed Collagen, Cocodimonium Hydroxypropyl Hydrolyzed Hair Keratin, Cocodimonium Hydroxypropyl Hydrolyzed Keratin, Cocodimonium Hydroxypropyl Hydrolyzed Rice Protein, Cocodimonium Hydroxypropyl Hydrolyzed Silk, Cocodimonium Hydroxypropyl Hydrolyzed Soy Protein, Cocodimonium Hydroxypropyl Hydrolyzed Wheat Protein, Cocodimonium Hydroxypropyl Silk Amino Acids, Hydroxypropyl Arginine Lauryl/Myristyl Ether HCl, Hydroxypropyltrimonium Gelatin, Hydroxypropyltrimonium Hydrolyzed Casein, Hydroxypropyltrimonium Hydrolyzed Collagen, Hydroxypropyltrimonium Hydrolyzed Conchiolin Protein, Hydroxypropyltrimonium Hydrolyzed Keratin, Hydroxypropyltrimonium Hydrolyzed Rice Bran Protein, Hydroxypropyltrimonium Hydrolyzed Silk, Hydroxypropyltrimonium Hydrolyzed Soy Protein, Hydroxypropyl Hydrolyzed Vegetable Protein, Hydroxypropyltrimonium Hydrolyzed Wheat Protein, Hydroxypropyltrimonium Hydrolyzed Wheat Protein/Siloxysilicate, Laurdimonium Hydroxypropyl Hydrolyzed Soy Protein, Laurdimonium Hydroxypropyl Hydrolyzed Wheat Protein, Laurdimonium Hydroxypropyl Hydrolyzed Wheat Protein/Siloxysilicate, Lauryldimonium Hydroxypropyl Hydrolyzed Casein, Lauryldimonium Hydroxypropyl Hydrolyzed Collagen, Lauryldimonium Hydroxypropyl Hydrolyzed Keratin, Lauryldimonium Hydroxypropyl Hydrolyzed Silk, Lauryldimonium Hydroxypropyl Hydrolyzed Soy Protein, Steardimonium Hydroxypropyl Hydrolyzed Casein, Steardimonium Hydroxypropyl Hydrolyzed Collagen, Steardimonium Hydroxypropyl Hydrolyzed Keratin, Steardimonium Hydroxypropyl Hydrolyzed Rice Protein, Steardimonium Hydroxypropyl Hydrolyzed Silk, Steardimonium Hydroxypropyl Hydrolyzed Soy Protein, Steardimonium Hydroxypropyl Hydrolyzed Vegetable Protein, Steardimonium Hydroxypropyl Hydrolyzed Wheat Protein, Steartrimonium Hydroxyethyl Hydrolyzed Collagen, Quaternium-76 Hydrolyzed Collagen, Quaternium-79 Hydrolyzed Collagen, Quaternium-79 Hydrolyzed Keratin, Quaternium-79 Hydrolyzed Milk Protein, Quaternium-79 Hydrolyzed Silk, Quaternium-79 Hydrolyzed Soy Protein, Quaternium-79 Hydrolyzed Wheat Protein.

The proportion by weight of the protein hydrolysate(s) in the total weight of the cosmetic agents is preferably 0.01 to 5% by weight, more preferably 0.025 to 3% by weight and in particular 0.05 to 2% by weight.

Suitable cationic polymers are for example:
quaternized cellulose derivatives, such as those available commercially under the names Celquat® and Polymer JR®,
quaternized cellulose derivatives which may be hydrophobically modified, for example Polyquaternium-67,
cationic alkyl polyglucosides,
cationized honey, for example the commercial product Honeyquat® 50,
cationic guar derivatives, such as in particular the products sold under the trade names Cosmedia® Guar N-Hance® and Jaguar®,
polymeric dimethyl diallyl ammonium salts and copolymers thereof with esters and amides of acrylic acid and methacrylic acid. The products available commercially under the names Merquat® 100 (poly(dimethyl diallyl ammonium chloride)) and Merquat® 550 (dimethyl diallyl ammonium chloride acrylamide copolymer) are examples of such cationic polymers,
copolymers of vinyl pyrrolidone with quaternized derivatives of dialkyl aminoalkyl acrylate and methacrylate, such as for example vinyl pyrrolidone-dimethyl aminoethyl methacrylate copolymers quaternized with diethyl sulfate. Such compounds are available commercially under the names Gafquat® 734 and Gafquat® 755,
vinyl pyrrolidone-vinyl imidazolium methochloride copolymers, such as those sold under the names Luviquat® FC 370, FC 550, FC 905 and HM 552,
quaternized polyvinyl alcohol,
as well as the polymers known under the names
Polyquaternium-2, Polyquaternium-17, Polyquaternium-18, Polyquaternium-24, Polyquaternium-27, Polyquaternium-32, Polyquaternium-37, Polyquaternium-74 and Polyquaternium-89.

Preferred further cationic polymers are preferably selected from the polymers known under the INCI names Guar Hydroxypropyltrimonium Chloride, Polyquaternium-67, Polyquaternium-10, Polyquaternium-6, Polyquaternium-7 and/or Polyquaternium-37. Particular preference is given to the polymers known under the INCI names Guar Hydroxypropyltrimonium Chloride and Polyquaternium-10.

The proportion by weight of the further cationic polymer(s) in the total weight of the cosmetic agents is preferably 0.01 to 5% by weight, more preferably 0.025 to 4% by weight, particularly preferably 0.05 to 3% by weight and in particular 0.1 to 2% by weight.

Suitable vitamins are understood to mean preferably the following vitamins, provitamins and vitamin precursors as well as derivatives thereof:

Vitamin A: the group of substances classed as vitamin A includes retinol (vitamin $A_1$) and 3,4-didehydroretinol (vitamin $A_2$). β-Carotene is the provitamin of retinol. Suitable vitamin A components are for example vitamin A acid and esters thereof, vitamin A aldehyde and vitamin A alcohol and esters thereof such as the palmitate and the acetate.

Vitamin B: the vitamin B group or vitamin B complex includes inter alia
Vitamin $B_1$ (thiamine)
Vitamin $B_2$ (riboflavin)
Vitamin $B_3$. The compounds nicotinic acid and nicotinamide (niacinamide) are often included under this designation.
Vitamin $B_5$ (pantothenic acid and panthenol). In the context of this group, use is preferably made of panthenol. Derivatives of panthenol which can be used are in particular the esters and ethers of panthenol, pantolactone as well as cationically derivatized panthenols. Individual representatives are, for example, panthenol triacetate, panthenol monoethyl ether and the monoacetate thereof, as well as cationic panthenol derivatives.
Vitamin $B_6$ (pyridoxine as well as pyridoxamine and pyridoxal).

Vitamin C (ascorbic acid): use in the form of the palmitic acid ester, glucosides or phosphates may be preferred. Use in combination with tocopherols may likewise be preferred.

Vitamin E (tocopherols, in particular α-tocopherol).

Vitamin F: the term "vitamin F" is usually understood to mean essential fatty acids, in particular linoleic acid, linolenic acid and arachidonic acid.

Vitamin H: the compound (3aS,4S,6aR)-2-oxohexahydrothienol[3,4-d]imidazole-4-valeric acid is designated as vitamin H, for which the trivial name biotin has become accepted.

Particular preference is given to vitamins, provitamins and vitamin precursors from groups A, B, E and H. Nicotinamide, biotin, pantolactone and/or panthenol are preferred in particular.

The proportion by weight of the vitamin(s), vitamin derivative(s) and/or vitamin precursor(s) in the total weight of the cosmetic agents is preferably 0.001 to 2% by weight, particularly preferably 0.005 to 1% by weight and in particular 0.01 to 0.5% by weight. Suitable oil, wax and/or fat components may preferably be selected from mineral, natural and synthetic oil components and/or fatty substances.

As natural (plant) oils, use is usually made of triglycerides and mixtures of triglycerides. Preferred natural oils are coconut oil, (sweet) almond oil, walnut oil, peach kernel oil, apricot kernel oil, avocado oil, tea tree oil, soybean oil, sesame oil, sunflower oil, tsubaki oil, evening primrose oil, rice bran oil, palm kernel oil, mango kernel oil, lady's smock oil, thistle oil, macadamia nut oil, grape seed oil, amaranth seed oil, argan oil, bamboo oil, olive oil, wheatgerm oil, pumpkin seed oil, mallow oil, hazelnut oil, safflower oil, canola oil, sasanqua oil, jojoba oil, rambutan oil, cocoa butter and shea butter.

As mineral oils, use may be made in particular of mineral oils, paraffin and isoparaffin oils and synthetic hydrocarbons. One example of a hydrocarbon which can be used is for example 1,3-di-(2-ethylhexyl)cyclohexane (Cetiol® S), which is available as a commercial product. A dialkyl ether may also be used as the oil component.

Dialkyl ethers which can be used are in particular di-n-alkyl ethers having in total between 12 and 36 C atoms, in particular 12 to 24 C atoms, such as for example di-n-octyl ether, di-n-decyl ether, di-n-nonyl ether, di-n-undecyl ether, di-n-dodecyl ether, n-hexyl n-octyl ether, n-octyl n-decyl ether, n-decyl n-undecyl ether, n-undecyl n-dodecyl ether and n-hexyl n-undecyl ether as well as di-tert-butyl ether, diisopentyl ether, di-3-ethyl decyl ether, tert-butyl n-octyl ether, isopentyl n-octyl ether and 2-methyl pentyl n-octyl ether.

Particular preference is given to di-n-octyl ether, which is available commercially under the name Cetiol® OE. As synthetic oils, use may preferably be made of silicone compounds.

Silicones have excellent conditioning properties on the hair. In particular, they give rise to a better combability of the hair in the wet and dry state and in many cases have a positive effect on the feel of the hair and the softness of the hair.

It is therefore desirable to use silicones in cosmetic hair treatment agents. Suitable silicones may be selected from:
(i) polyalkylsiloxanes, polyarylsiloxanes, polyalkylarylsiloxanes, which are volatile or non-volatile, straight-chain, branched or cyclic, crosslinked or uncrosslinked;
(ii) polysiloxanes which in their general structure include one or more organofunctional groups selected from:
   a) substituted or unsubstituted aminated groups;
   b) (per)fluorinated groups;
   c) thiol groups;
   d) carboxylate groups;
   e) hydroxylated groups;
   f) alkoxylated groups;
   g) acyloxyalkyl groups;
   h) amphoteric groups;
   i) bisulfate groups;
   j) hydroxyacyl amino groups;
   k) carboxyl groups
   l) sulfonic acid groups; and
   m) sulfate or thiosulfate groups;
(iii) linear polysiloxane (A)-polyoxyalkylene (B) block copolymers of type $(A-B)_n$, where n>3;
(iv) grafted silicone polymers having a non-silicone-containing, organic framework consisting of an organic main chain formed from organic monomers that include no silicone, onto which at least one polysiloxane macromer has been grafted in the chain and optionally on at least one chain end;
(v) grafted silicone polymers having a polysiloxane framework, onto which non-silicone-containing, organic monomers have been grafted which have a polysiloxane main chain onto which at least one organic macromer that includes no silicone has been grafted in the chain and optionally on at least one of the ends thereof;
(vi) or mixtures thereof.

Fatty substances are to be understood to mean fatty acids, fatty alcohols and natural and synthetic waxes, which may be present both in solid form and liquid in aqueous dispersion.

As fatty acids, use may be made of linear and/or branched, saturated and/or unsaturated fatty acids having 6-30 carbon atoms. Preference is given to fatty acids having 10-22 carbon atoms. Among these, mention may be made for example of the isostearic acids, such as the commercial products Emersol® 871 and Emersol® 875, and isopalmitic acids, such as the commercial product Edenor® IP 95, and also all other fatty acids sold under the trade names Edenor® (Cognis). Other typical examples of such fatty acids are caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselinic acid, linoleic acid, linolenic acid, eleostearic acid, arachidic acid, gadoleic acid, behenic acid and erucic acid, as well as the technical mixtures thereof.

Particular preference is usually given to the fatty acid fractions obtainable from coconut oil or palm oil; the use of stearic acid is generally particularly preferred.

As fatty alcohols, use may be made of saturated, mono- or polyunsaturated, branched or unbranched fatty alcohols having $C_6$-$C_{30}$, preferably $C_{10}$-$C_{22}$ and very particularly preferably $C_{12}$-$C_{22}$ carbon atoms. Use may be made for example of decanol, octanol, octenol, dodecenol, decenol, octadienol, dodecadienol, decadienol, oleyl alcohol, erucic alcohol, ricinoleic alcohol, stearyl alcohol, isostearyl alcohol, cetyl alcohol, lauryl alcohol, myristyl alcohol, arachidyl alcohol, caprylic alcohol, capric alcohol, linoleyl alcohol, linolenyl alcohol and behenyl alcohol, and Guerbet alcohols thereof, this list being intended to be of exemplary and non-limiting nature. However, the fatty alcohols originate from preferably natural fatty acids, it usually being possible to start from an isolation from the esters of the fatty acids by reduction. According to the invention, use may also be made of those fatty alcohol fractions which are produced by reducing naturally occurring triglycerides such as beef tallow, palm oil, peanut oil, rapeseed oil, cottonseed oil, soybean oil, sunflower oil and linseed oil, or fatty acid esters which are produced from the transesterification products thereof with suitable alcohols, and thus represent a mixture of different fatty alcohols. Such substances can be purchased for example under the names Stenol®, for example Stenol® 1618, or Lanette®, for example Lanette® O, or Lorol®, for example Lorol® C8, Lorol® C14, Lorol® C18, Lorol® C8-18, HD-Ocenol®, Crodacol®, for example Crodacol® CS, Novol®, Eutanol® G, Guerbitol® 16, Guerbitol® 18, Guerbitol® 20, Isofol® 12, Isofol® 16, Isofol® 24, Isofol® 36, Isocarb® 12, Isocarb® 16 or Isocarb® 24. Of course, wool wax alcohols such as those which can be purchased under the names Corona®, White Swan®, Coronet® or Fluilan®, can also be used according to the invention.

As natural or synthetic waxes, use may be made of solid paraffins or isoparaffins, carnauba wax, beeswax, candelilla wax, ozokerite, ceresin, spermaceti, sunflower wax, fruit waxes such as apple wax or citrus wax for example, and microwaxes of PE or PP. Such waxes are available for example from the company Kahl & Co., Trittau.

Further fatty substances are for example
   ester oils. Ester oils are to be understood to mean the esters of $C_6$-$C_{30}$ fatty acids with $C_2$-$C_{30}$ fatty alcohols. Preference is given to the monoesters of fatty acids with alcohols having 2 to 24 C atoms. Examples of fatty acid components used in the esters are caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselinic acid, linoleic acid, linolenic acid, eleostearic acid, arachidic acid, gadoleic acid, behenic acid and erucic acid and technical mixtures thereof.

Examples of the fatty alcohol components in the ester oils are isopropyl alcohol, caproic alcohol, caprylic alcohol, 2-ethylhexyl alcohol, capric alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linolyl alcohol, linolenyl alcohol, eleostearyl alcohol, arachyl alcohol, gadoleyl alcohol, behenyl alcohol, erucyl alcohol and brassidyl alcohol and technical mixtures thereof. Particular preference is given to isopropyl myristate (Rilanit® IPM), isononanoic acid C16-18 alkyl ester (Cetiol® SN), 2-ethylhexyl palmitate (Cegesoft® 24), stearic acid 2-ethylhexyl ester (Cetiol® 868), cetyl oleate, glycerol tricaprylate, coconut fatty alcohol caprinate/caprylate (Cetiol® LC), n-butyl stearate, oleyl erucate (Cetiol® J 600), isopropyl palmitate (Rilanit® IPP), oleyl oleate (Cetiol®), lauric acid hexyl ester (Cetiol® A), di-n-butyl adipate (Cetiol® B), myristyl myristate (Cetiol® MM), cetearyl isononanoate (Cetiol® SN), oleic acid decyl ester (Cetiol® V).

dicarboxylic acid esters such as di-n-butyl adipate, di-(2-ethylhexyl) adipate, di-(2-ethylhexyl) succinate and diisotridecyl acetate and also diol esters such as ethylene glycol dioleate, ethylene glycol diisotridecanoate, propylene glycol di-(2-ethyl hexanoate), propylene glycol diisostearate, propylene glycol dipelargonate, butanediol diisostearate, neopentyl glycol dicaprylate, symmetrical, asymmetrical or cyclic esters of carbonic acid with fatty alcohols, glycerol carbonate or dicaprylyl carbonate (Cetiol® CC), ethoxylated or non-ethoxylated mono-, di- and tri-fatty acid esters of saturated and/or unsaturated linear and/or branched fatty acids with glycerol, such as for example Monomuls® 90-O18, Monomuls® 90-L12, Cetiol® HE or Cutina® MD.

The proportion by weight of the oil, wax and/or fat components in the total weight of the cosmetic agents is preferably 0.01 to 5% by weight, particularly preferably 0.025 to 4% by weight and in particular 0.05 to 3% by weight.

Particular preference is given to cosmetic cleansing agents which include, as an additional care component, at least one cationic polymer, at least one water-insoluble silicone compound and/or at least one vitamin (derivative).

Particular preference is given to a caring active ingredient complex which includes at least two care substances from the aforementioned active ingredient groups.

Glycerol may be added separately to cosmetic agents in an amount of up to 10% by weight (based on the total weight of the cleansing agent). However, it may also be a constituent of the aqueous-alcoholic carrier.

It has been found that the cosmetic agents according to the invention are also suitable for use as an anti-dandruff preparation.

The total weight of anti-dandruff agents in the total weight of the cosmetic agents may be preferably 0.01 to 10% by weight, more preferably 0.025 to 7.5% by weight, particularly preferably 0.05 to 5% by weight and in particular 0.075 to 3% by weight.

Suitable anti-dandruff active ingredients may be selected from piroctone olamine, climbazole, zinc pyrithione, ketoconazoles, salicylic acid, sulfur, selenium sulfide, tar preparations, undecenoic acid derivatives, burdock extracts, poplar extracts, stinging nettle extracts, walnut shell extracts, birch extracts, willow bark extracts, rosemary extracts and/or arnica extracts.

Preference is given to climbazole, zinc pyrithione and piroctone olamine.

Further active ingredients, auxiliaries and additives which may be included in the cosmetic agents according to the invention are for example:

plant extracts,
humectants,
perfumes,
UV filters,
thickening agents such as gelatins or plant gums, for example agar-agar, guar gum, alginates, xanthan gum, gum arabic, karaya gum, locust bean gum, linseed gums, dextrans, cellulose derivatives, for example methyl cellulose, hydroxyalkyl cellulose and carboxymethyl cellulose, starch fractions and derivatives such as amylose, amylopectin and dextrins, clays and phyllosilicates such as for example bentonite or fully synthetic hydrocolloids such as for example polyvinyl alcohol, the Ca, Mg or Zn soaps,
thickening agents such as acrylic and methacrylic (co) polymers, for example the crosslinked homopolymers of acrylic acid (INCI name: carbomer), which are also known as carboxyvinyl polymers. Such polyacrylic acids are available inter alia from the company 3V Sigma under the trade name Polygel®, for example Polygel DA, and from the company B. F. Goodrich under the trade name Carbopol®, for example Carbopol 940 (molecular weight approximately 4,000,000), Carbopol 941 (molecular weight approximately 1,250,000) or Carbopol 934 (molecular weight approximately 3,000,000). The following acrylic acid copolymers are also suitable for example:

a. copolymers of two or more monomers from the group consisting of acrylic acid, methacrylic acid and the simple esters thereof, preferably formed with $C_1$-$C_4$ alkanols (INCI name: Acrylates Copolymer), including for instance the copolymers of methacrylic acid, butyl acrylate and methyl methacrylate or of butyl acrylate and methyl methacrylate, and which are available for example from the company Rohm & Haas under the trade names Aculyn® and Acusol® and from the company Degussa (Goldschmidt) under the trade name Tego® Polymer, for example the anionic, non-associative polymers Aculyn 22, Aculyn 28, Aculyn 33 (crosslinked), Acusol 810, Acusol 820, Acusol 823 and Acusol 830;

b. crosslinked acrylic acid copolymers of high molecular weight, including for instance the copolymers of $C_{10}$-$C_{30}$ alkyl acrylates which are crosslinked with an allyl ether of sucrose or of pentaerythritol and which comprise one or more monomers from the group consisting of acrylic acid, methacrylic acid and the simple esters thereof, preferably formed with $C_1$-$C_4$ alkanols (INCI name: Acrylates-($C_{10}$-$C_{30}$)-Alkyl Acrylate Crosspolymer), and which are available for example from the company B. F. Goodrich under the trade name Carbopol®, for example the hydrophobicized Carbopol ETD 2020 and Carbopol 1382 (INCI Acrylates-($C_{10}$-$C_{30}$)-Alkyl Acrylate Crosspolymer) and Carbopol Aqua 30, texturizing agents such as maleic acid and lactic acid,
dimethyl isosorbide,
cyclodextrins,
active ingredients for improving the fiber structure, in particular mono-, di- and oligosaccharides such as for example glucose, galactose, fructose, fruit sugar and lactose,
dyes for coloring the agent,
substances for adjusting the pH, for example α- and β-hydroxycarboxylic acids such as citric acid, lactic acid, malic acid, glycolic acid,
active ingredients such as bisabolol,
complexing agents such as EDTA, NTA, β-alaninediacetic acid and phosphonic acids,
ceramides. Ceramides are understood to mean N-acyl sphingosine (fatty acid amides of sphingosine) or synthetic analogs of such lipids (known as pseudoceramides),
propellants such as propane-butane mixtures, $N_2O$, dimethyl ether, $CO_2$ and air,
antioxidants,
preservatives, such as for example sodium benzoate or salicylic acid,
additional viscosity adjusters such as salts (NaCl).

The cosmetic agents according to the invention may preferably have a pH in the range from 3 to 8, more preferably from 3.5 to 7.5, particularly preferably from 4 to 7 and in particular from 5 to 6.5.

The cosmetic agents according to the invention preferably have a viscosity in the range from 1000 to 15,000 mPas, preferably from 1500 to 12,500 mPas and in particular from 3000 to 10,000 mPas (in each case measured using a Haake rotational viscometer VT550; 20° C.; measuring device MV; spindle MV II; 8 rpm). Compositions having such a viscosity can readily distribute on the respective application surface—particularly preferably on the hair—and after being applied can optionally be rinsed off again with water.

EXAMPLES

The following hair cleansing agents according to the invention were prepared (compositions A-D in the following table; amounts specified in [% by weight]):

|  | A | B | C | D |
|---|---|---|---|---|
| Carbopol ETD 2020 ®[1] | 0.6 |  |  |  |
| Texapon N70 ®[2] |  |  |  | 10.0 |
| Iselux LQ ®[3] | 10.0 | 6.0 | 10.0 |  |
| Hostapon SCI 85C ®[4] |  | 4.0 | 4.0 |  |
| Rewoteric AM C ®[5] | 4.0 | 4.0 | 4.0 |  |
| Plantacare 818UP ®[6] | 1.5 | 1.5 | 1.5 | 1.5 |
| Tego Betain F50 ®[7] |  |  |  | 5.5 |
| Mirataine CBS ®[8] | 12.0 | 12.0 | 12.0 |  |
| Polymer JR 400 ®[9] | 0.4 | 0.4 | 0.4 | 0.4 |
| Styrene/Acrylates Copolymer | 1.0 | 1.0 | 1.0 | 1.0 |
| EDDS (Natrquest E30) | 0.7 | 0.7 | 0.7 |  |
| Abil ME 45 ®[10] | 1.0 | 1.0 | 1.0 | 1.0 |
| Antil 200 ®[11] | 2.5 | 2.5 | 2.5 | 2.5 |
| Preservative | q.s. | q.s. | q.s. | q.s. |
| Perfume | q.s. | q.s. | q.s. | q.s. |
| Citric acid/NaOH (pH 5.5-6.5) | q.s. | q.s. | q.s. | q.s. |
| Water | ad 100 | ad 100 | ad 100 | ad 100 |
| Appearance |  | white, milky |  |  |
| Viscosity* |  | 4000-8000 mPas |  |  |
| Determination of amount of foam | 3 | 2-3 | 2-3 | 2-3 |
| Feel of the foam in wet hair | 3 | 2 | 2-3 | 3 |
| Reduction in wet combability [%] | 35 | 43 | 51 | 38 |

*determined using a Haake rotational viscometer VT550; 20° C.; measuring device MV; spindle MV II; 8 rpm The following commercial products were used in compositions A-D:
[1]INCI name: ACRYLATES/C10-30 ALKYL ACRYLATE CROSSPOLYMER; Lubrizol
[2]INCI name: SODIUM LAURETH SULFATE; 70% AS; BASF
[3]INCI name: SODIUM LAUROYL METHYL ISETHIONATE; 32% AS; Innospec
[4]INCI name: DISODIUM COCOYL ISETHIONATE; 84% AS; Clariant
[5]INCI name: SODIUM COCOAMPHOACETATE; 50% AS; Evonik
[6]INCI name: COCO-GLUCOSIDE, AQUA; 51-53% AS; BASF
[7]INCI name: AQUA, COCAMIDOPROPYL BETAINE; 35-37.5% AS; Evonik
[8]INCI name: COCAMIDOPROPYL HYDROXYSULTAINE; 50% AS; Rhodia
[9]INCI name: Polyquaternium-10; Shanghai Jida meticulous Chemical Industry
[10]INCI name: SILICONE QUATERNIUM-22, POLYGLYCERYL-3 CAPRATE, DIPROPYLENE GLYCOL, COCAMIDOPROPYL BETAINE; Evonik
[11]INCI name: PEG-200 HYDROGENATED GLYCERYL PALMATE, PEG-7 GLYCERYL COCOATE; Evonik The results in the table show that the compositions (B, C) according to the invention form an amount of foam comparable to the amounts of foam customary in conventional surfactant systems for cosmetic cleansing agents (D). The foam properties of the compositions according to the invention are moreover better than the foam properties of comparable compositions which do not include the combination of surfactants a) and b).

Finally, the wet combability of hair treated with the cleansing agents according to the invention was able to be significantly improved.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A cosmetic cleansing agent including, in a suitable carrier,
   a) at least one isethionate selected from the group consisting of sodium cocoyl isethionate and sodium lauroyl isethionate, and
   b) at least one anionic surfactant selected from the group consisting of sodium lauroyl methyl isethionate and sodium cocoyl methyl isethionate,
   c) 1 to 15 wt. % cocamidopropyl hydroxysultaine;
   d) at least one alkyl (oligo)glucoside of general formula RO-[G]$_x$, in which R represents an alkyl and/or alkenyl radical having 4 to 24 C atoms, G represents a sugar residue having 5 or 6 C atoms, and x represents numbers from 1 to 10, wherein the proportion by weight of the alkyl (oligo)glucoside in the total weight of the composition is 0.5 to 10% by weight; and
   e) at least one animal protein hydrosylate selected from the group consisting of elastin, collagen, keratin, and silk protein hydrolysates,
   wherein the cosmetic cleansing agent includes the surfactants a) and b) in a weight ratio of 1:1 to 2:1.

2. The cosmetic cleansing agent according to according to claim 1, wherein the proportion by weight of the anionic surfactants a) and b) in the total weight of the composition is 0.5 to 20%.

3. The cosmetic cleansing agent according to claim 1, wherein the proportion by weight of the surfactant a) in the total weight of the cleansing agents is 0.5 to 20% by weight, the proportion by weight of the surfactant b) in the total weight of the cleansing agents is 0.5 to 20% by weight, and the proportion by weight of the surfactant according to formula (II) in the total weight of the cleansing agents is 1 to 15% by weight.

4. The cosmetic cleansing agent according to claim 1, wherein the proportion by weight of the isethionate a) in the total weight of the cleansing agents is 0.5 to 20% by weight, and the proportion by weight of the isethionate b) in the total weight of the cleansing agents is 0.5 to 20% by weight.

5. The cosmetic cleansing agent according to claim 1, further including at least one chelating agent, wherein the concentration by weight of the chelating agent in the total weight of the composition is 0.01 to 3%.

6. The cosmetic cleansing agent according to claim 5, wherein the chelating agent is one or more selected from the group consisting of ethylenediaminetetraacetic acid (EDTA) and ethylenediamine disuccinate (EDDS).

7. The cosmetic cleansing agent according to claim 1, wherein the proportion by weight of surfactants that include sulfate groups in the total weight of the composition is less than 0.5% by weight.

* * * * *